US008777876B2

(12) United States Patent
Swann

(10) Patent No.: US 8,777,876 B2
(45) Date of Patent: *Jul. 15, 2014

(54) METHODS AND APPARATUS FOR DETERMINING FALLOPIAN TUBE OCCLUSION

(71) Applicant: Betsy Swann, Grass Valley, CA (US)

(72) Inventor: Betsy Swann, Grass Valley, CA (US)

(73) Assignee: Bayer Essure Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/042,047

(22) Filed: Sep. 30, 2013

(65) Prior Publication Data

US 2014/0031634 A1 Jan. 30, 2014

Related U.S. Application Data

(63) Continuation of application No. 12/577,108, filed on Oct. 9, 2009, now Pat. No. 8,585,616.

(51) Int. Cl.
A61B 5/00 (2006.01)
A61B 5/103 (2006.01)
A61B 5/117 (2006.01)
A61M 29/00 (2006.01)
A61M 31/00 (2006.01)
A61M 37/00 (2006.01)

(52) U.S. Cl.
USPC ........... 600/591; 600/561; 600/587; 606/193; 604/93.01; 604/94.01; 604/101.01

(58) Field of Classification Search
None
See application file for complete search history.

(56) References Cited

U.S. PATENT DOCUMENTS

| | | |
|---|---|---|
| 4,693,704 A | 9/1987 | Ogita |
| 5,104,377 A | 4/1992 | Levine |
| 5,188,595 A | 2/1993 | Jacobi |
| 5,487,390 A | 1/1996 | Cohen et al. |
| 5,503,626 A | 4/1996 | Goldrath |
| 5,522,961 A | 6/1996 | Leonhardt |
| 5,547,656 A | 8/1996 | Unger |
| 5,558,857 A | 9/1996 | Klaveness et al. |
| 5,562,099 A | 10/1996 | Cohen et al. |
| 5,567,413 A | 10/1996 | Klaveness et al. |
| 5,569,449 A | 10/1996 | Klaveness et al. |
| 5,571,497 A | 11/1996 | Unger |
| 5,676,925 A | 10/1997 | Klaveness et al. |
| 5,718,884 A | 2/1998 | Klaveness et al. |
| 5,795,562 A | 8/1998 | Klaveness et al. |
| 5,800,493 A | 9/1998 | Stevens et al. |
| 5,911,252 A | 6/1999 | Cassel |

(Continued)

FOREIGN PATENT DOCUMENTS

| | | |
|---|---|---|
| WO | WO 99/07420 A1 | 2/1999 |
| WO | WO 2008/073916 A2 | 6/2008 |
| WO | WO 2010/040046 A1 | 4/2010 |

OTHER PUBLICATIONS

Hilgers, M.D., Thomas W., et al., "Intratubal pressure before and after transcervical catheterization of the fallopian tubes," Fertility and Sterility, vol. 72, No. 1, Jul. 1999, pp. 174-178.

(Continued)

Primary Examiner — Brian Szmal
Assistant Examiner — Megan Leedy
(74) Attorney, Agent, or Firm — Blakely, Sokoloff, Taylor & Zafman LLP

(57) ABSTRACT

Devices and methods for determining fallopian tube occlusion. The methods may include determining fallopian tube occlusions through a pressurization or volumetric determination.

12 Claims, 15 Drawing Sheets

(56) References Cited

U.S. PATENT DOCUMENTS

| | | | |
|---|---|---|---|
| 5,919,434 | A | 7/1999 | Dugstad et al. |
| 5,935,098 | A | 8/1999 | Blaisdell et al. |
| 5,935,137 | A | 8/1999 | Saadat et al. |
| 6,001,335 | A | 12/1999 | Unger |
| 6,012,342 | A | 1/2000 | Blight et al. |
| 6,024,722 | A | 2/2000 | Rau et al. |
| 6,024,939 | A | 2/2000 | Unger |
| 6,080,129 | A | 6/2000 | Blaisdell |
| 6,106,806 | A | 8/2000 | Klaveness et al. |
| 6,110,444 | A | 8/2000 | Klaveness et al. |
| 6,165,442 | A | 12/2000 | Swaerd-Nordmo et al. |
| 6,290,672 | B1 | 9/2001 | Abae |
| 6,526,979 | B1 | 3/2003 | Nikolchev et al. |
| 6,528,039 | B2 | 3/2003 | Unger |
| 6,585,687 | B1 | 7/2003 | Shkolnik |
| 6,634,361 | B1 | 10/2003 | Nikolchev et al. |
| 6,709,667 | B1 | 3/2004 | Lowe et al. |
| 6,773,696 | B2 | 8/2004 | Unger |
| 8,048,086 | B2 | 11/2011 | Lee-Sepsick et al. |
| 8,052,669 | B2 | 11/2011 | Lee-Sepsick et al. |
| 2001/0024639 | A1 | 9/2001 | Unger |
| 2001/0039440 | A1 | 11/2001 | Lasheras et al. |
| 2003/0060800 | A1 | 3/2003 | Ryan |
| 2004/0163655 | A1 | 8/2004 | Gelfand et al. |
| 2004/0223914 | A1 | 11/2004 | Unger |
| 2005/0171419 | A1 | 8/2005 | De Ziegler |
| 2005/0240211 | A1 | 10/2005 | Sporri et al. |
| 2006/0293560 | A1 | 12/2006 | Nguyen et al. |
| 2008/0167664 | A1 | 7/2008 | Payne et al. |
| 2008/0249534 | A1 | 10/2008 | Gruber et al. |
| 2009/0306538 | A1 | 12/2009 | Siminou |
| 2010/0086492 | A1 | 4/2010 | Lee-Sepsick et al. |
| 2010/0179394 | A1 | 7/2010 | Sohn et al. |
| 2011/0094519 | A1 | 4/2011 | Gopal et al. |
| 2011/0137150 | A1 | 6/2011 | Connor et al. |

OTHER PUBLICATIONS

Karande, Vishvanath C., "The assessment of tubal functional status by tubal perfusion pressure measurements" Human Reproduction Update 1996, vol. 2, No. 5 pp. 429-433, European Society for Human Reproduction and Embryology.

Kiyokawa, K., et al., "Three-dimensional hysterosalpingo-contrast sonography (3D-HyCoSy) as an outpatient procedure to assess infertile women: a pilot study" Ultrasound in Obstetrics & Gynecology, vol. 16, Issue 7, p. 648, Dec. 2000.

Novy, Miles J., et al., "Diagnosis of corneal obstruction by transcervical fallopian tube cannulation" Fertility and Sterility, vol. 50, No. 3, Sep. 1988, The American Fertility Society, pp. 434-440.

Papaioannou, Spyros, et al., "The potential value of tubal perfusion pressures measured during selective salpingography in predicting fertility" Human Reproduction, vol. 18, No. 2 Feb. 2003, pp. 358-363. Accessed online at http://humrep.oxfordjournals.org/cgi/content/full/18/2/358.

PCT International Preliminary Report on Patentability for International Application No. PCT/US2010/051515, mailed Apr. 19, 2012 (9 pages).

PCT International Search Report and Written Opinion for International Application No. PCT/US2010/051515, mailed Dec. 13, 2010, 14 pages.

Prefumo, F., et al., "The sonographic evaluation of tubal patency with stimulated acoustic emission imaging" Ultrasound in Obstetrics & Gynecology, vol. 20, Issue 4, p. 386, Oct. 2002.

Schlief, R., et al., "Basic properties and results of clinical trials of ultrasound contrast agents based on galactose" Ann Acad Med Singapore, Sep. 1993;22(5):762-7.

Subramaniam, R., et al., "The Role of Three-dimensional Ultrasonography in Gynaecology" JPOG, Jan./Feb. 2005, pp. 27-36.

Wittmer, Michael H., et al., "Hysterosalpingography for Assessing Efficacy of Essure Microinsert Permanent Birth Control Device" American Journal of Roentgenology, Clinical Observations, vol. 187, No. 4, Oct. 2006, pp. 955-958. Accessed online at http://www.ajronline.org/cgi/content/full/187/4/955.

Wolf et al., "The current state of hysterosalpingography" Radiographics, 8(6):1041-1058, Nov. 1988.

METHODS AND APPARATUS FOR DETERMINING FALLOPIAN TUBE OCCLUSION

RELATED APPLICATIONS

The present application is a continuation of U.S. patent application Ser. No. 12/577,108, filed on Oct. 9, 2009, which is incorporated herein by reference.

BACKGROUND OF THE INVENTION

1). Field of the Invention

The field of the invention relates to methods and apparatuses for determining fallopian tube occlusion.

2). Discussion of Related Art

Female sterilization prevents pregnancy by occluding or mechanically blocking the fallopian tubes. There are several different occlusion techniques—tubes can be tied or "ligated," blocked with mechanical devices such as clips or rings, or scarred closed with electric current.

In partial salpingectomy, the fallopian tubes are cut and tied with suture material. The Pomeroy technique, a widely used version of partial salpingectomy, involves tying a small loop of the tube and cutting off the top segment of the loop.

Clips are used to block the fallopian tubes by clamping down and cutting off the blood supply to a portion of the tubes, causing a small amount of scarring or fibrosis that prevents fertilization from occurring. The two most common clips are the Filshie clip, made of titanium, and the Wolf clip (also known as the Hulka clip), made of plastic. Clips are simple to use, but each type requires a special applicator.

Tubal rings, like clips, also block the tubes mechanically. A very small loop of the fallopian tube is pulled through the stretched ring. When the ring is released, it stops the blood supply to that small loop. The resulting scarring blocks passage of the sperm or egg. The Yoon Ring, made of silicone, is widely used.

Electrocoagulation uses electric current to coagulate or burn a small portion of each fallopian tube. Unipolar coagulation passes current through the forceps applied on the tubes, and the current leaves a woman's body through an electrode placed under her thigh. In bipolar coagulation, current enters and leaves a woman through two ends of the forceps.

Occlusion device applied transcervically such as the ESSURE ® device manufactured by CONCEPTUS, INC. are also used to permanently block the fallopian tubes.

Hysterosalpingography (HSG) is a known method for determining whether a fallopian tube has been successfully occluded. In HSG, the uterus is pressurized with a fluoroscopically visual fluid. A radiologist fluoroscopically monitors the fallopian tubes to see if the fluid escapes past the occluded portion. Fluid seen escaping and filling the fallopian tubes, for example near the ovaries would indicate that the fallopian tubes are not occluded and that the patient may still be fertile. HSG is problematic in that it requires a radiologist to be present and also requires the use of specialized equipment. Thus HSG also cannot be performed in a doctor's office.

SUMMARY OF THE DESCRIPTION

The invention includes in one embodiment a method to detect fallopian tube occlusion, including visually identifying the cornua of a fallopian tube through a transcervical approach, wherein the fallopian tube was subjected to a procedure to attempt to occlude the fallopian tube, coupling a device to a cornua to fluidly separate the cornua from the remainder of the uterus, pressurizing the cornua, and monitoring the pressurization of the cornua to determine if the fallopian tube is occluded.

The device may be coupled to the cornua by an inflatable member of the device.

The inflatable member may be coupled to the cornua by applying force against the cornua.

The inflatable member may be coupled to the cornua by a applying a vacuum between the inflatable member and the cornua.

The cornua may be inflated to a pressure greater than 500 mmHg.

The method may be used with no fluoroscopic visualization of the procedure.

The inflatable member is configured to separate the first cornua and a second cornua from the remainder of the uterus by occupying a uterine cavity.

The inflatable member has at least one first lumen that is configured to pressurize the first cornua, the at least one first lumen extending through the inflatable member to align with the first fallopian tube. The inflatable member has at least one second lumen that is configured to pressurize the second cornua. The at least one second lumen extends through the inflatable member to align with a second fallopian tube and is capable of being activated simultaneously with the at least one first lumen.

The invention includes in one embodiment a method to determine fallopian tube occlusion, comprising distending a uterus with a first fluid, the uterus including at least one fallopian tube and cornua of the fallopian tube, wherein the fallopian tube was subjected to a procedure to attempt to occlude the fallopian tube, visually identifying the cornua of a fallopian tube through a transcervical approach, coupling a device to the cornua to fluidly separate a sealed portion of the cornua from the remainder of the uterus, applying a vacuum to the sealed portion of the cornua to evacuate a first fluid in the sealed portion of the cornua, pressurizing the cornua with a second fluid, and monitoring the volume of the cornua to determine if the fallopian tube is occluded.

The device may be coupled to the cornua by an inflatable member of the device.

The inflatable member may be coupled to the cornua by applying force against the cornua.

The inflatable member may be coupled to the cornua by a applying a vacuum between the inflatable member and the cornua.

The cornua may be inflated to a pressure greater than 500 mmHg.

The second fluid may be visually differentiated from the first fluid.

The method may additionally include visually confirming that the second fluid does not leak into the first fluid past the device.

The first fluid removed from the cornua portion may be measured.

The fallopian tube may be determined to be permanently occluded by the implanted occlusion device by determining if there is more of the second fluid inserted in the evacuated portion of the cornua than of the first fluid removed from the evacuated portion of the cornua.

The second fluid may be non-soluble with the first fluid.

The method may be used with no fluoroscopic visualization of the procedure.

BRIEF DESCRIPTION OF THE DRAWINGS

The invention is further described by way of example(s) with reference to the accompanying drawings, wherein.

DETAILED DESCRIPTION OF THE INVENTION

Figure 1:
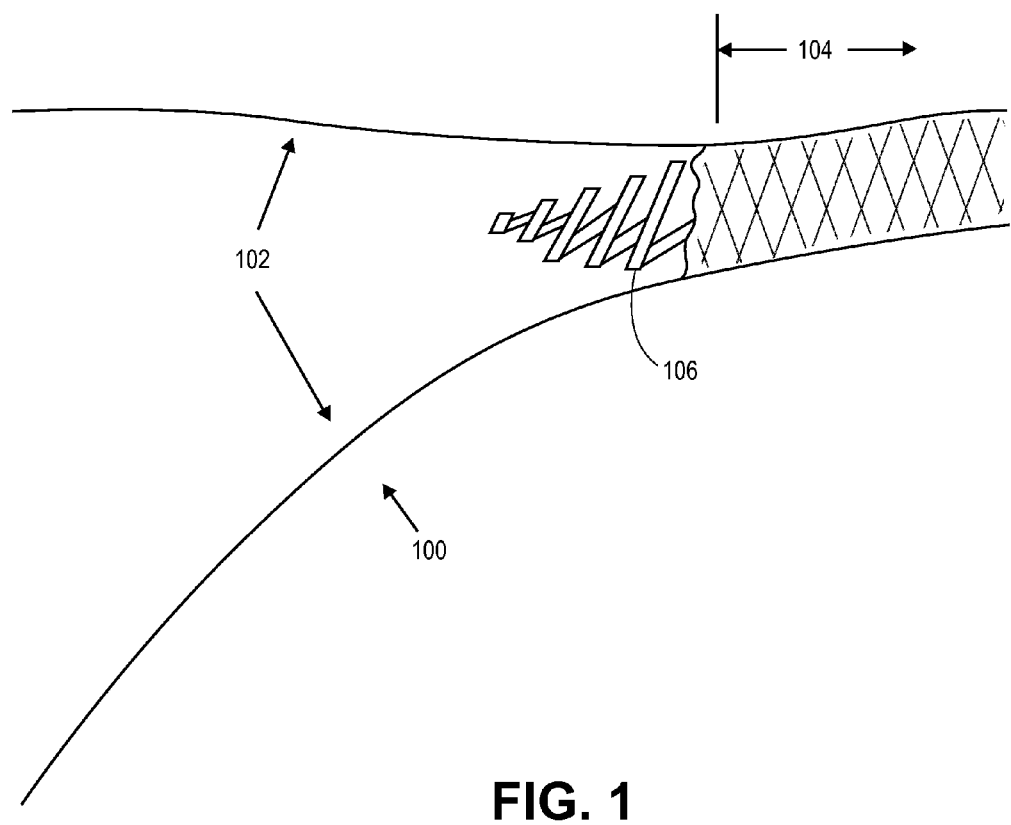
FIG. 1 is a cross section of a uterus including a utero-tubal junction and cornua, and a previously implanted fallopian tube occlusion device.

FIG. 1 shows a cross section 100 of an ostium or cornua 102 of a uterus. The ostium or cornua 102 is considered to be the flower like opening of a fallopian tube and lies between the greater uterus and the utero-tubal junction 104 (hereinafter, "UTJ"). A previously placed implant 106 is shown placed in the UTJ. The function of the implant is to serve as a platform for encouraging tissue growth occlusion, as shown by the cross-hatched area. When the UTJ has been fully occluded by tissue growth, typically 3 months after implantation, the fallopian tube will no longer be viable for fertilization. The fallopian tube may also be sealed by other known operations, such as partial salpingectomy, electro-cauterization, or clips or rings applied externally to the fallopian tube. The methods and apparatuses described herein apply equally to all forms of tubal ligation.

The implant 106 includes a proximal portion that extends into the ostium or cornua 102. The proximal portion of the implant 106 serves as a visual indicator of the placement of the implant 106. Devices such as the ESSURE ® device manufactured by CONCEPTUS, INC. include tail like visual indicators. Not all fallopian tube implants include such indicators. Even with a visual indicator, which shows only positive placement, the device may not fully occlude the utero-tubal junction 104.

Figure 2A:
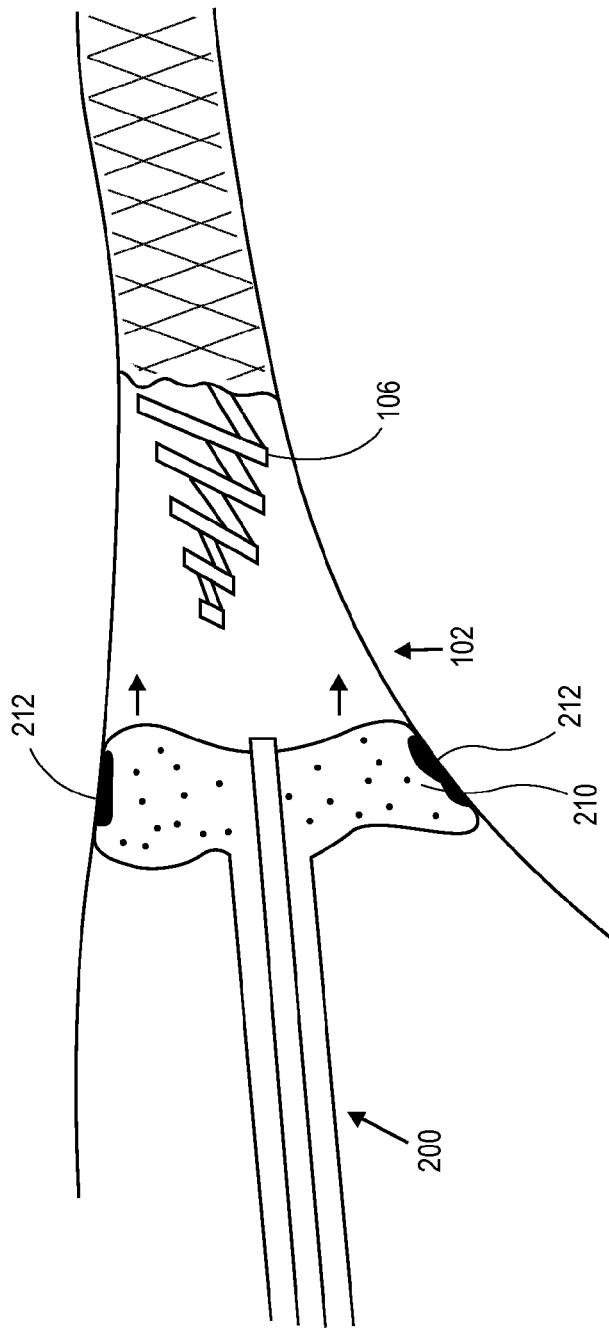
FIGS. 2A-2C show cross sections of a uterus including a utero-tubal junction and cornua, and a previously implanted fallopian tube occlusion device and a method to determine if the fallopian tube is fully occluded.

FIG. 2A illustrates one embodiment of the invention for determining whether a fallopian tube is occluded. The fallopian tube shows a previously placed occlusion device 106. A device 200 is shown coupled to the ostium or cornua 102 of a uterus. The device 200 may be delivered to the ostium or cornua 102 by a hysteroscope which is transcervically approached through the vagina of the patient. The uterus is also typically distended with a working fluid, such as saline. The cornua 102 is visually identified using an image provided by hysteroscope, which may also be coupled to a monitor.

As shown, the device 200 includes an a sealing member 210 to fluidly seal and separate a portion of the ostium or cornua 102 from the remainder of the uterus to create a sealed region. The sealing member 210 is preferably inflatable, although this is not a requirement of this embodiment of the invention. Force is applied by the operator of the device 200 to seal the sealing member 210 against the ostium or cornua 102. In one embodiment, the sealing member 210 has an inflated diameter of the cornua 102 so that a sealed region is created regardless of the expansion and contractions of the cornua 102.

In one embodiment, the sealing member 210 includes a biocompatible adhesive 212 capable of creating a seal between the sealing member 210 and the endometrium of the uterus. In one embodiment, the biocompatible adhesive 212 is located along an outer circumference of the sealing member 210 between the sealing member 210 and endometrial layer. It is understood that the adhesive 212 may be strategically applied in specific locations around the sealing member 210 circumference to ensure the sealing member 210 engages with the endometrium. It is also understood that the biocompatible adhesive 212 can be any known adhesive such as wet adhesives, synthetic, natural, bio-adhesives, hydrogels, resins or any other adhesive suitable for application in the uterus.

In one embodiment, the adhesive 212 is a temporary adhesive application and may remove a portion of the endometrium upon removal of the sealing member 210. However, the adhesive 212 should not cause the removal of any portion of the myometrium upon removal of the sealing member 210.

Figure 2B:
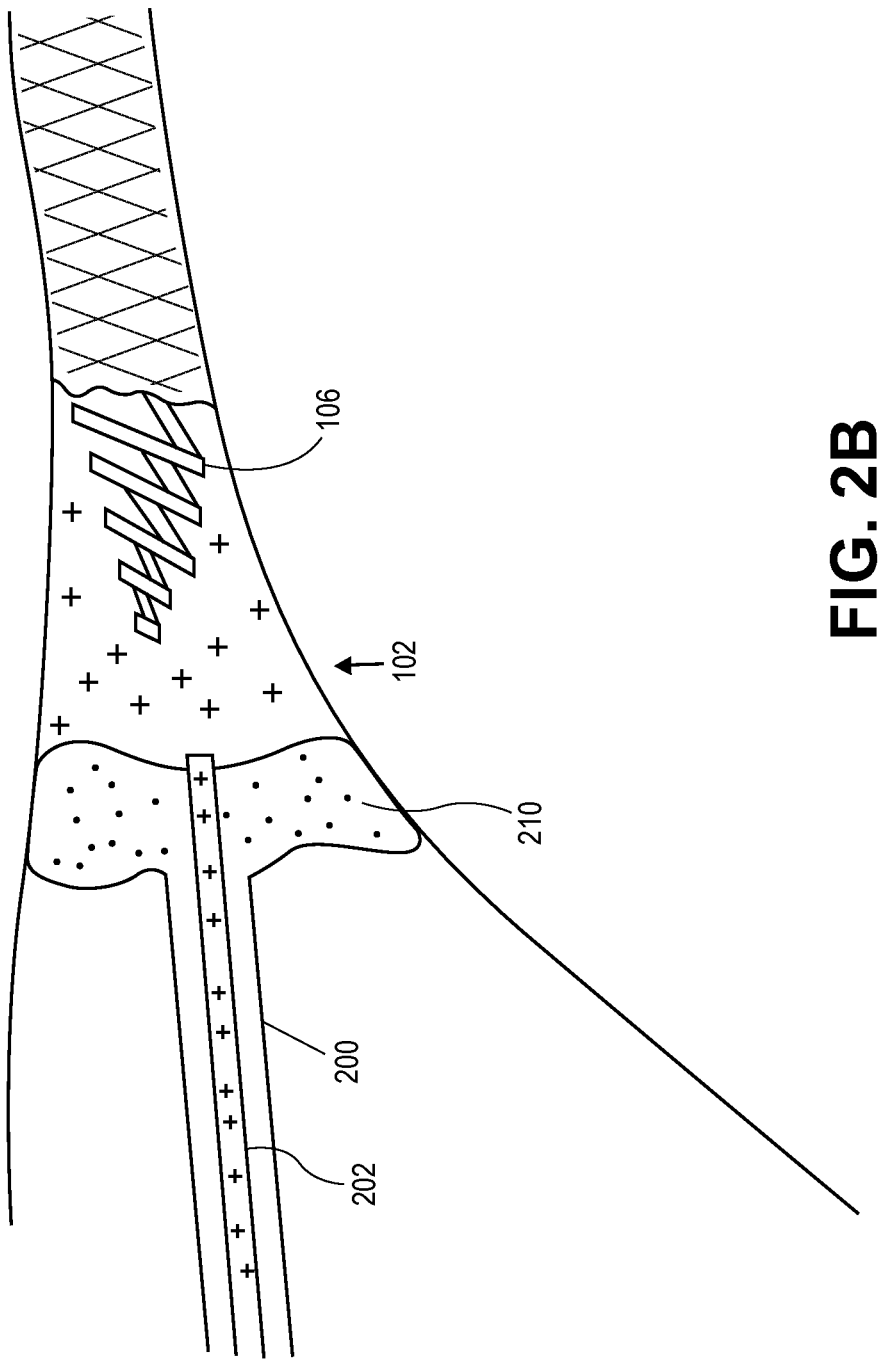

FIG. 2B shows the device 200 applying a positive pressure through lumen 210, as shown by the "+" marks, within a sealed portion of the cornua 102. A pressure monitor, such as a pressure gauge, is also coupled to the lumen 210. Pressure is applied for a set amount of time, for example 30 seconds to 3 minutes, to determine if the sealed portion will hold pressure. If the sealed portion is able to maintain a desired amount of pressure for a predetermined amount of time, one may be able to positively determine whether the fallopian tube is fully occluded. A pressure drop will show that the fallopian tube is not fully occluded.

The amount of pressure applied must be large enough to determine whether the fallopian tube is positively occluded. The fallopian tube may also be naturally and temporarily blocked. Past tests have determined that as much as 500 mmHg is required to remove a temporary blockage from a fallopian tube. In another embodiment, a minimum pressure is about 50 mmHg while a maximum pressure is about 350 mmHg. In one embodiment, an ideal range of pressure is about 90-120 mmHg. Care should be taken such that enough pressure is applied to the cornua 102 to determine whether the fallopian tube is positively occluded while preserving the temporarily blocked fallopian tube. Pressures greater than 500 mmHg may be applied in order to determine intentional fallopian tube occlusion, for example 700-2000 mmHg.

This method is advantageous over previous method of determining whether a fallopian tube is occluded by previously implanted occlusion devices. Previous methods required pressurization of the entire uterus with a fluoroscopically visible fluid, known as Hysterosalpingography (HSG). A radiologist monitored the fallopian tubes via an x-ray device to determine if the fluoroscopically visible fluid leaks past the previously implanted occlusion devices. This prior art procedure is costly, because it requires the presence of a radiologist and specialized x-ray equipment. The current invention does not require fluoroscopic visualization of the procedure, and may be performed with a less specialized environment, such as a doctor's office. The sealing member 210 may also include an adhesive as previously described above.

Figure 2C:
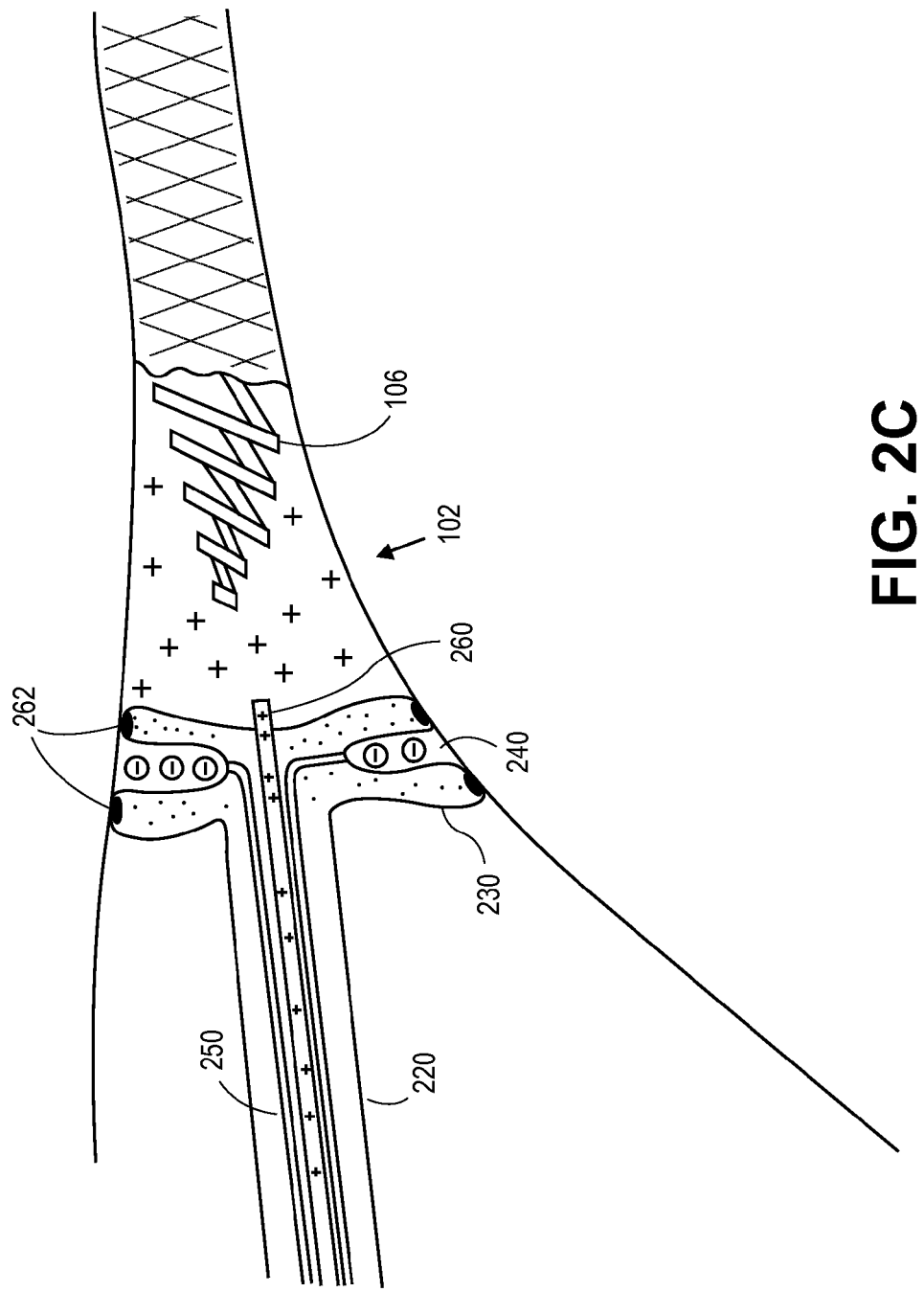

FIG. 2C shows an alternative embodiment of a method for determining whether a fallopian tube is occluded. The fallopian tube shows a previously placed occlusion device 106. A device 220 is shown coupled to the ostium or cornua 102 of a uterus. The device 220 may be delivered to the ostium or cornua 102 by a hysteroscope which is transcervically approached through the vagina of the patient. The uterus is also typically distended with a working fluid, such as saline. The cornua is visually identified using an image provided by hysteroscope, which may also be coupled to a monitor.

As shown, the device 220 includes an a sealing member 230 to fluidly seal and separate a portion of the cornua from the remainder of the uterus. The sealing member 230 is preferably inflatable, although this is not a requirement of this embodiment of the invention. The sealing member 230 features sealing chambers 240 circumferentially surrounding the sealing member 230. The sealing member may be defined by two prominent sections of the sealing member 230. A vacuum is applied through vacuum lumens 250 to positively seal the sealing member to the cornua 102. A vacuum source (not shown) as known to one commonly skilled in the art, such as a pump, is also coupled to the vacuum lumens 250.

FIG. 2C shows the device 200 applying a positive pressure through lumen 260, as shown by the "+" marks, within sealed portion of the cornua. A pressure monitor (not shown) as commonly known to ones skilled in the art, such as a pressure gauge, is also coupled to the lumen 260. Pressure is applied for a set amount of time, for example 30 seconds to 3 minutes, to determine if the sealed portion will hold pressure. If the sealed portion is able to maintain a desired amount of pressure for a predetermined amount of time, one may be able to positively determine whether the fallopian tube is fully occluded. A pressure drop will show that the fallopian tube is not fully occluded.

This method is particularly advantageous because it allows an operator remove his hands from device 220, while simultaneously maintaining a positive seal against the cornua. In one embodiment, a bio-adhesive 262 may located on circumferential portions of the prominent sections of the sealing member 230 to ensure a sealed engagement between the sealing member 230 and the endometrium.

Figure 3A:
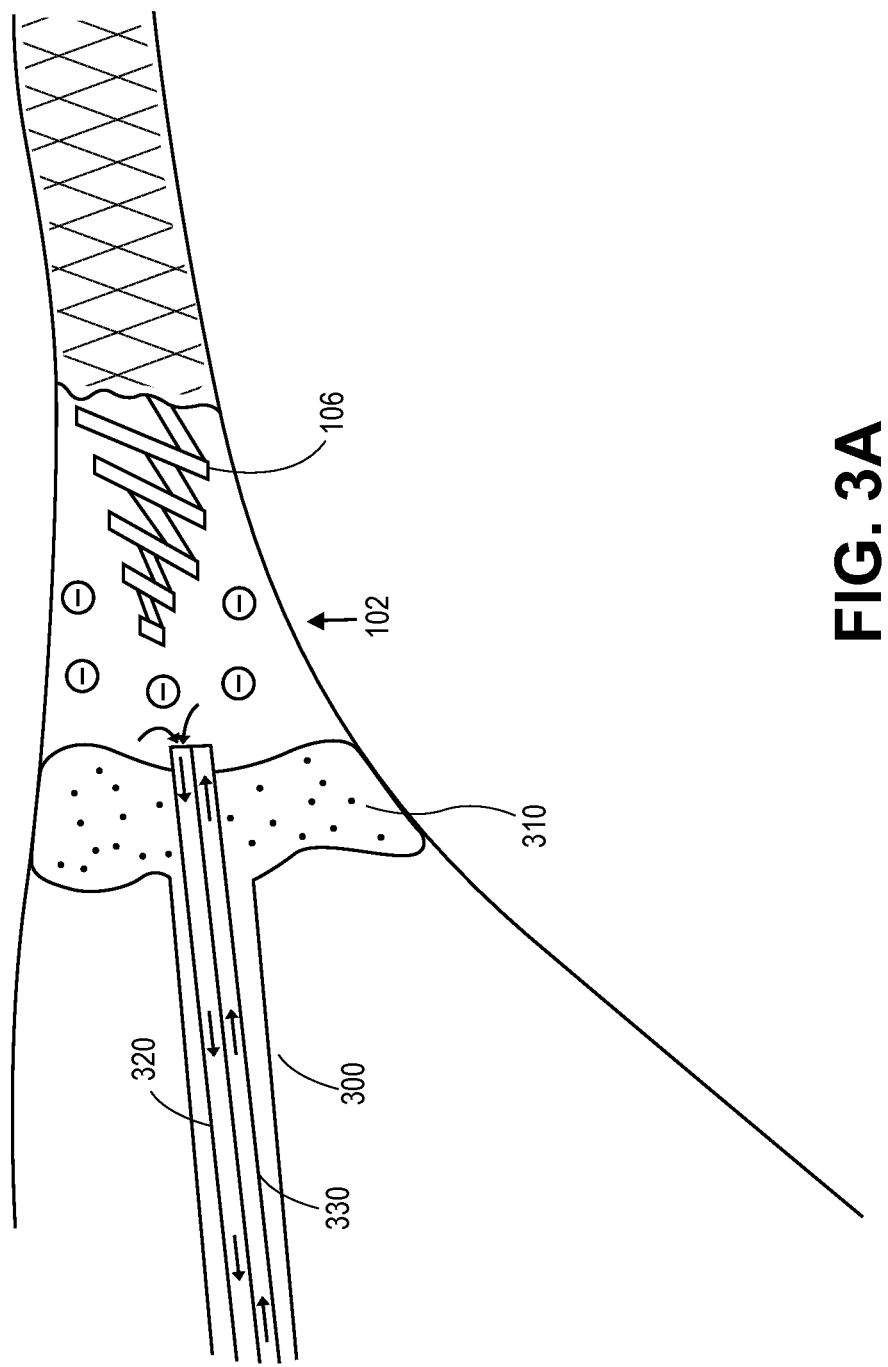
FIGS. 3A and 3B show cross sections of a uterus including a utero-tubal junction and cornua, and a previously implanted fallopian tube occlusion device and a method to determine if the fallopian tube is fully occluded.

FIG. 3A illustrates one embodiment of the invention for determining whether a fallopian tube is occluded. The fallopian tube shows a previously placed occlusion device 106. A device 300 is shown coupled to the cornua 102 of a uterus. The device 300 may be delivered to the cornua by a hysteroscope which is transcervically approached through the vagina of the patient. The uterus is also typically distended with a working fluid, such as saline. The cornua is visually identified using an image provided by hysteroscope, which may also be coupled to a monitor.

As shown, the device 300 includes a sealing member 310 to fluidly seal and separate a portion of the cornua from the remainder of the uterus. The sealing member 310 is preferably inflatable, although this is not a requirement of this embodiment invention. Force is applied by the operator of the device 300 to seal the sealing member 310 against the cornua 102. Alternatively the device 300 may use a vacuum to seal the sealing member 310 against the cornua such as shown in FIG. 2C.

FIG. 3A shows the device 200 applying a negative pressure through a first lumen 320, as shown by the "−" marks, within the sealed portion of the cornua. Distension fluid is then evacuated from the sealed portion and measured using a measuring device as known to one commonly skilled in the art, such as a marked syringe. The amount of fluid evacuated will typically be small, for example 1 cc or less, given that the volume of the sealed cornua is small.

Figure 3B:
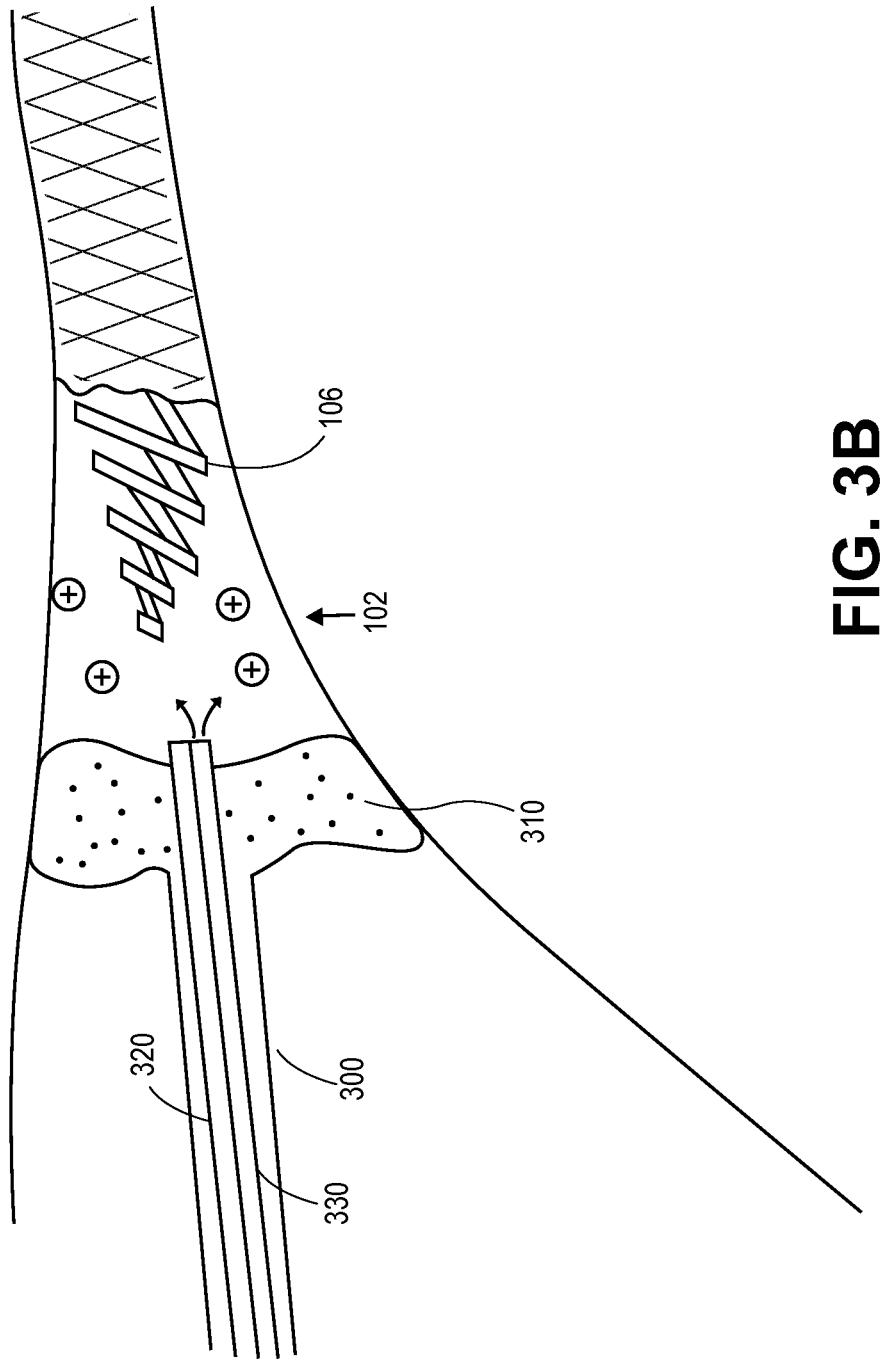

FIG. 3B shows a second lumen 330 supplying a second fluid to replace the distension fluid. The second fluid is pressurized in a device as described in FIGS. 2A-2C, however it is not necessary to monitor the pressure. The pressure may be mechanically set by a pressure source as known to one commonly skilled in the art, such as a syringe or pump coupled to a lockable leur, which is in turn coupled to lumen 330.

The volume of the second fluid applied is measured to determine if it is greater than the amount of distension fluid removed. If the volumes are equal or close, for example within 10%, then the fallopian tube is determined to be positively occluded by the occlusion device I.

If the volume of the second fluid is significantly greater than the amount removed, for example more than 20%, then the second fluid likely leaked past the utero-tubal junction and occlusion device 106. Thus it follows that the occlusion device is not fully occluding the utero-tubal junction. The volume of the lumen 330 should be considered when calculating the volume of the second fluid applied into the evacuated portion of the cornua.

The second fluid may be visually differentiated from the distension fluid, for example colored with a green dye. This aids in visually determining if any leaks exist between the sealing member 310 and cornua. The second fluid may also be non-soluble along with the distension fluid, for example biocompatible vegetable or mineral oil. In that case, both the distension fluid and second fluid may be measured using the same container, e.g. a single syringe, without intermixing between the fluids.

This method is advantageous over previous method of determining whether a fallopian tube is occluded by previously implanted occlusion devices. Previous methods required pressurization of the entire uterus with a fluoroscopically visible fluid, known as Hysterosalpingography (HSG). This embodiment does not require fluoroscopic visualization of the procedure, and may be performed with a less specialized environment, such as a doctor's office.

Figure 4A:
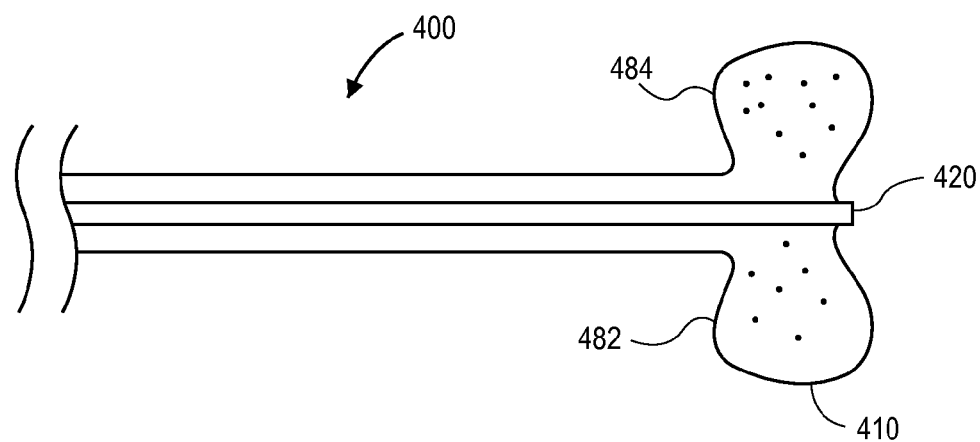
FIGS. 4A-4C show cross sections of devices which may be used to determine if a fallopian tube is fully occluded.

FIG. 4A shows one embodiment of a catheter 400 for use in methods described herein. The catheter includes an inflatable member 410, and a lumen 420 for pressurizing a cornua of a fallopian tube. The inflatable member 410 may be characterized as a circular shaped balloon. Balloon catheters, materials, and methods of construction are well known in the art, for example as shown in U.S. Patents: U.S. Pat. Nos. 5,522,961, 6,585,687, and 6,024,722, all of which are respectively incorporated herein by reference in their respective entirety. Appropriate coupling devices, such as leurs (not shown) are coupled to the proximal portion of the catheter 400 for adding suitable pressures or vacuums to inflatable member 440 and the remaining lumens. The catheter is of a suitable working length for use in a transcervical environment, for example 400 mm.

In one embodiment, a back portion 482 of the inflatable member 410 is a concave shape. In another embodiment, the back portion 484 of the inflatable member 410 is a convex shape. A specific concave or convex shape can be selected depending on the curvature of the cornua.

Figure 4B:
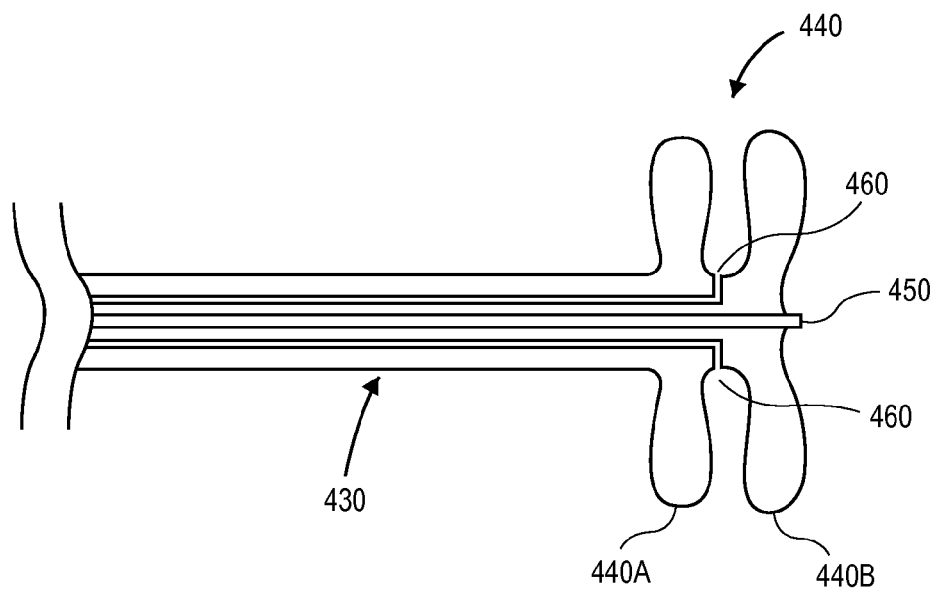
Figure 4C:
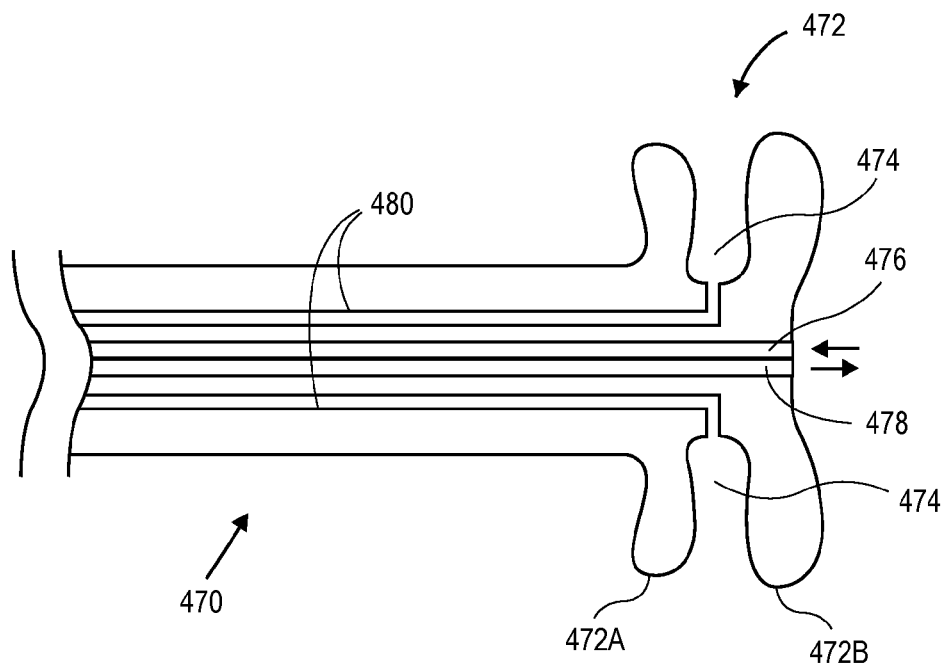

FIG. 4B shows one embodiment of a catheter 430 for use in methods described herein. The catheter includes an inflatable member 440, and a lumen 450 for pressurizing a cornua of a fallopian tube. It is understood that the lumen 450 can also include a first and second lumen, as shown in FIG. 4C. The inflatable member 440, may be characterized as a circular shaped balloon with at least two prominent sections 440*a* and 440*b*. A vacuum space exists between sections 440*a* and 440*b* for application of a vacuum by lumens 460 for sealing the inflatable member to a cornua of a fallopian tube. Appropriate coupling devices, such as leurs (not shown) are coupled to the proximal portion of the catheter 430 for adding suitable pressures or vacuums to inflatable member 440 and the remaining lumens. The catheter is of a suitable working length for use in a transcervical environment, for example 400 mm.

FIG. 4C shows one embodiment of a catheter 470, and a first 476 and second 478 lumen, similar to the embodiment shown in FIG. 3A. Again, the inflatable member 472 is characterized by a circular shape and two prominent radial portions 472*a*, 472*b* extending in a perpendicular direction transverse to the longitudinal axis of the first 476 and second lumen 478. The first 472*a* and second 472*b* prominent portions form a circular vacuum space 474 which will engage the cornual wall, as already described. A vacuum suction is created within the vacuum space 474 through the vacuum lumen 480. The same fluid distension technique can be applied to the catheter 470 through the first 476 and second 478 lumen, as already described in FIGS. 3A and 3B.

Figure 5A:
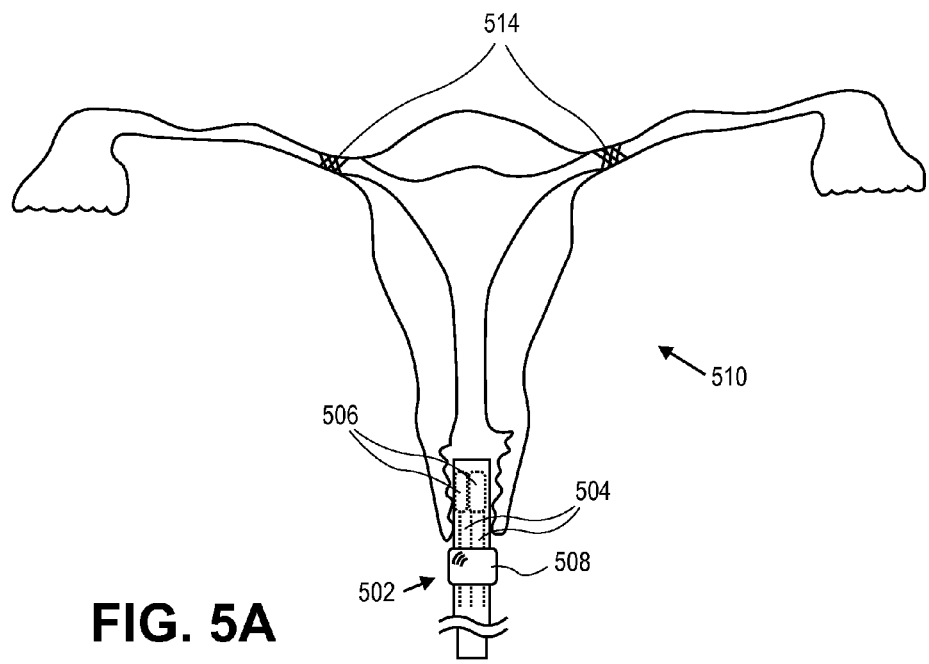
FIGS. 5A-5D show cross sections of a uterus including a utero-tubal junction and cornua, and a method to determine if the fallopian tube is fully occluded, according to another embodiment.

FIG. 5A shows an arrangement 500 having an outer catheter or sheath 502 with a proximal end and a distal end being inserted into a uterus 510 with previously occluded portions 514. The sheath 502 is made from a material such as stainless steel, Teflon, silicone, or other known materials and may be flexible or rigid. In one embodiment, the sheath 502 can have a length in a range of about 12 cm to about 25 cm and a diameter in a range of 0.4 cm to about 0.8 cm.

The sheath 502 contains two inner catheters 504. The two inner catheters 504 are shown in a collapsed position within the outer sheath 502 with respective balloon end portions 506 located near the distal end of the sheath 502. As shown, the balloon end portions 506 are not inflated when located within the outer catheter or sheath 502.

In addition, an outer sheath balloon 508 is connected with the outer sheath 502. The outer sheath balloon 508 remains in a deflated configuration upon insertion of the outer sheath 502 into the cervix.

Figure 5B:
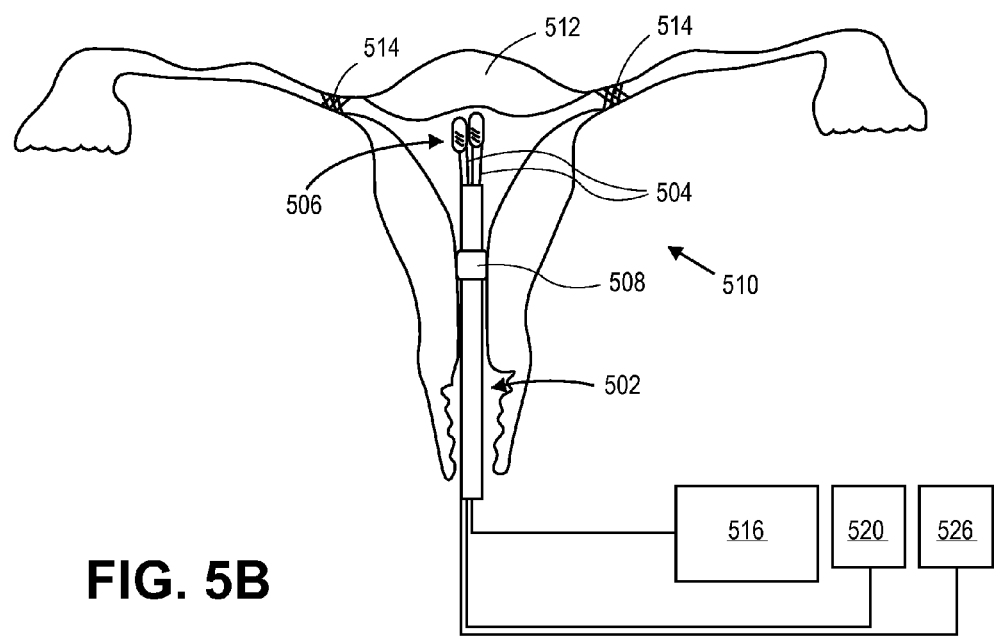

FIG. 5B shows the outer sheath 502 being inserted into the uterus so that a distal portion of the outer sheath 502 is located near the fundus region 512 of the uterus 510. The inner catheters 504 are exposed by either advancing the inner catheters 504 or by retracting the outer sheath 502. The balloon end portions 506 are in a deflated configuration when the inner catheters 504 are in a collapsed position. Upon reaching a desired position, FIG. 5B illustrates the outer sheath balloon 508 being inflated to engage the walls of the cervical canal to create a sealed upper region of the uterus 510. The engagement of the outer sheath balloon 508 prevents unwanted movement during subsequent procedures. The outer sheath balloon 508 is connected with a first air or fluid source 516 for inflating the outer sheath balloon 508. The sheath 502 is also connected with a second air or fluid source 520 and a vacuum source 526 as will be discussed in further detail.

Figure 5C:
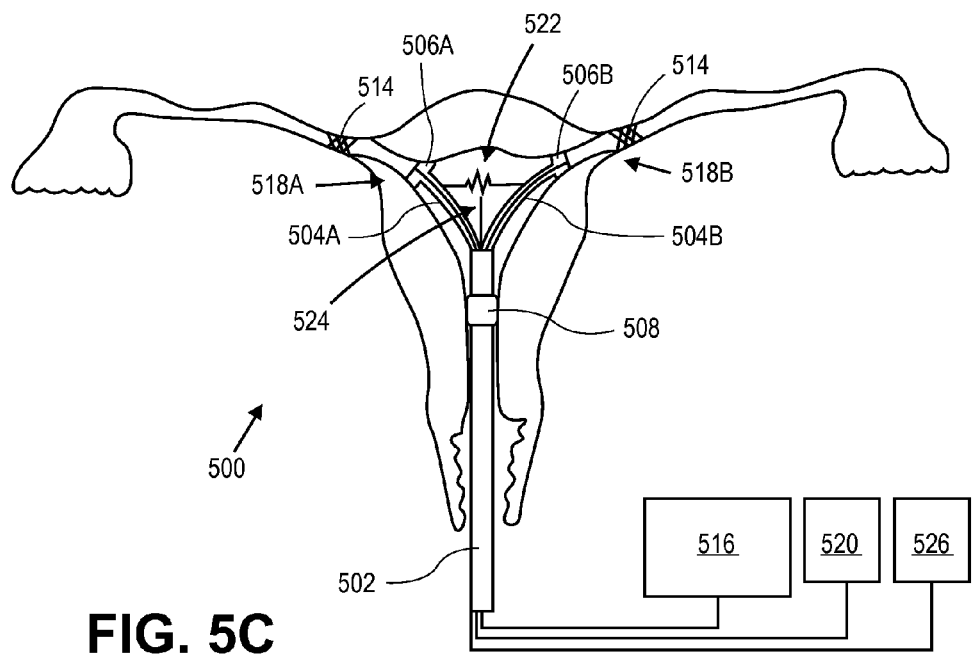

FIG. 5C shows the inner catheters 504 being moved from a collapsed position to an open and extended Y-shaped position. The first catheter 504*a* is movable to seal a first cornua 518*a* and the second catheter 504*b* is movable to seal a second cornua 518*b*. The inner catheters 504 can be configured to create pressure within a respective cornua region 518 according to any of the embodiments previously described. Moreover, the inner catheters 504 can be configured to apply a fluid distension technique according to any of the embodiments already described.

FIG. 5C further shows a first balloon end portion 506*a* being inflated by the first air or fluid source 516. In one embodiment, the air or fluid source can be a single source that can selectively allow air or fluid to flow to the outer sheath balloon 508 or the end balloon portions 506 through the use of a valve (not shown). It is understood that, in one embodiment, the outer sheath balloon 508 may not be necessary and may be removed or inactivated. In another embodiment, separate air or fluid sources may be used. In one embodiment, a separate air or fluid source 520 is provided to apply pressure or fluid distension to the cornua regions 518*a*, 518*b* through lumens within the inner catheters 504 as already described. In one embodiment, the air source 520 is a hand pump with a gauge of pressure. In another embodiment, the fluid source 520 is a syringe.

In one embodiment, a spring mechanism 522 is biased to expand the inner catheters 504 to an open Y-position. A wire 524 is connected with the spring mechanism 522 to activate or retract the spring mechanism 522 so that the inner catheters 504 can move from an open Y-position to a closed collapsed position. In one embodiment, the user may pull on the wire 524 to cause the spring mechanism 522 to retract causing the inner catheters 504 to collapse. It is understood that a spring mechanism that expands upon pulling of the wire 524 may be provided.

Figure 5D:
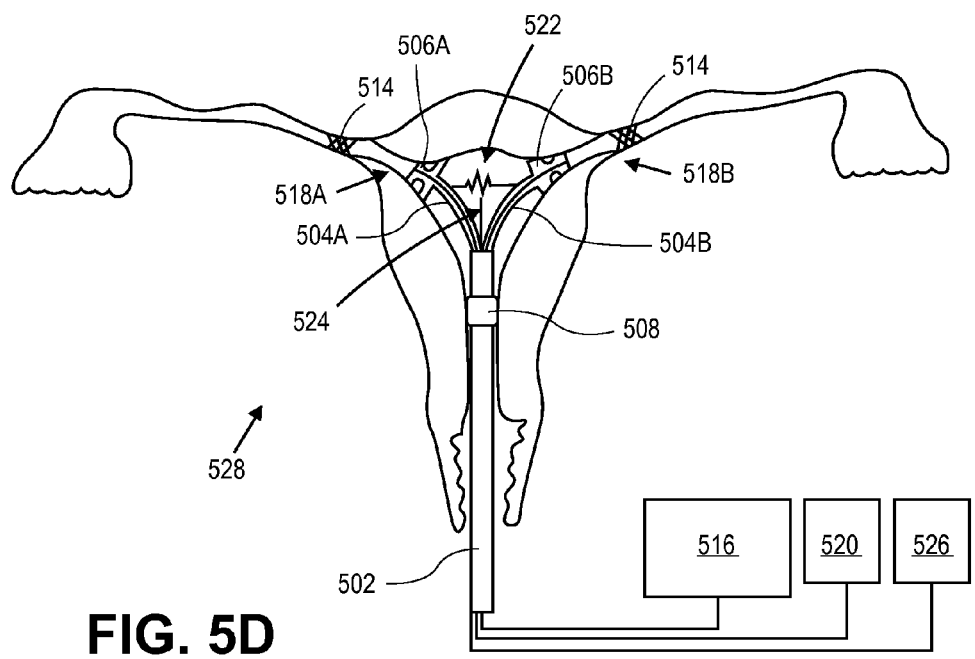

FIG. 5D further shows an embodiment 528 similar to FIG. 5C. However, the end balloon portions 506 have a vacuum cavity as described in FIGS. 2C, 4B, and 4C. The vacuum cavity engages the cornual walls and creates a sealed region for determining whether a fallopian tube is patent as previously described. A vacuum is created within the vacuum cavity through a vacuum source 526 and lumens within the catheter as previously described. The vacuum source 526 can also be utilized to deflate the outer sheath balloon 508 and end balloon portions 506 to a collapsed position for withdrawal from the uterus. A collapsed withdrawal position would be similar to the insertion configuration shown in FIG. 5A.

Figure 6A:
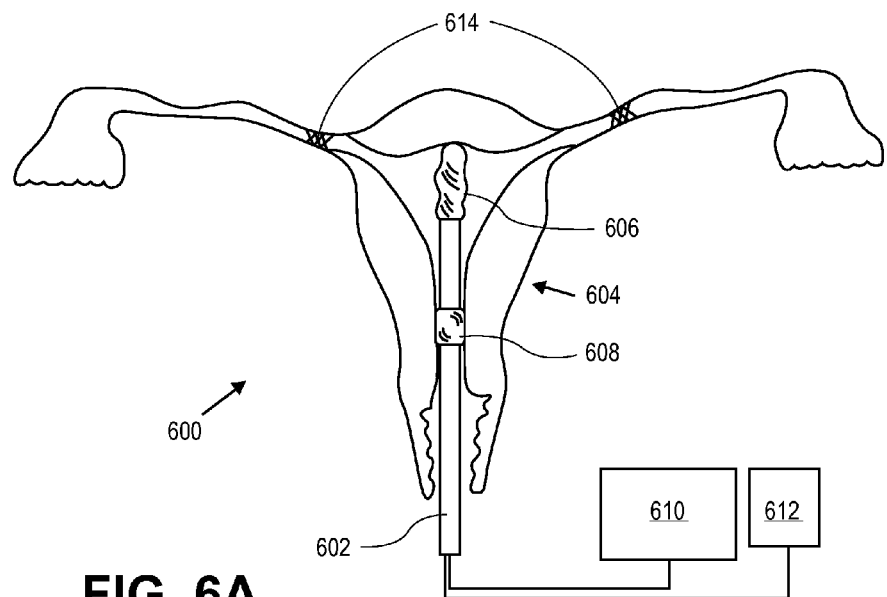
FIGS. 6A and 6B show cross sections of a uterus including a utero-tubal junction and cornua, and a method to determine if the fallopian tube is fully occluded, according to another embodiment.

FIG. 6A shows another embodiment 600 where a catheter or sheath 602 having similar dimensions as already described is inserted into the uterus 604 having occluded regions 614. The sheath 602 has a proximal end and a distal end. FIG. 6A further shows the proximal end of the catheter including a uterine balloon 606 in a collapsed position. An outer sheath balloon 608 is shown in a collapsed position located at a mid-portion of the sheath 602. In a collapsed position, the uterus balloon 606 is inserted through the cervix and into the uterus toward the fundus region. The uterine balloon 606 is connected with an air or fluid source 610 through a lumen of the catheter 602. The uterine balloon 606 is also connected with a vacuum source 612 through a catheter lumen. It is understood that the outer sheath balloon 608 may be connected with the same air or fluid source 610 and vacuum source 612 for selective inflation and collapse. In one embodiment, the outer sheath balloon 608 may be inflated or collapsed independently from the uterine balloon 606.

Figure 6B:
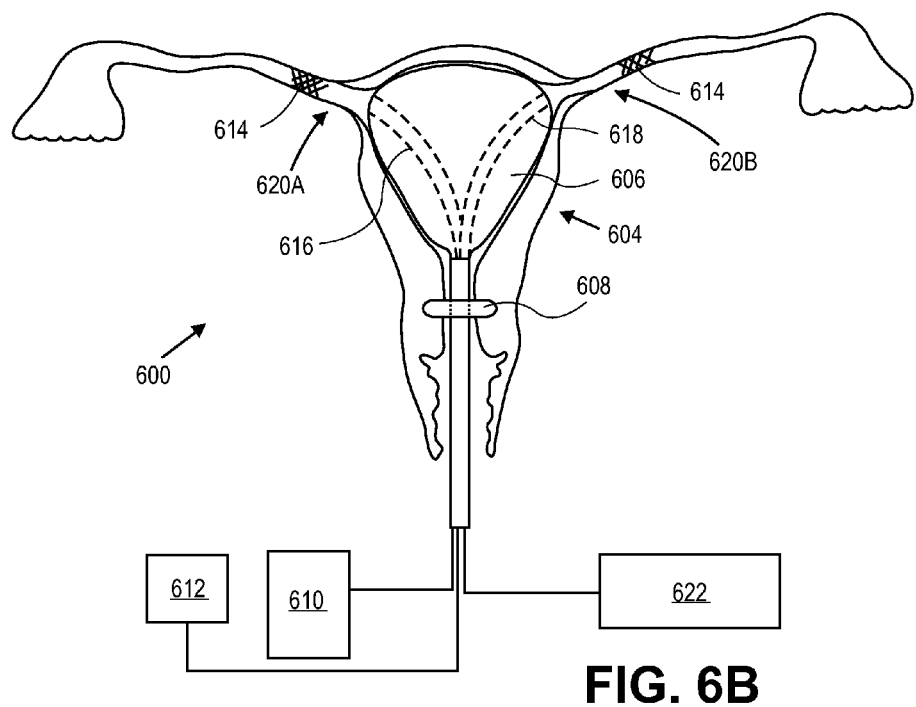

FIG. 6B shows the same embodiment described in FIG. 6A when the uterine balloon 606 and outer sheath balloon 608 are expanded. It is understood that the outer sheath balloon 608 may be removed or inactive, according to one embodiment. However, as shown in FIG. 6B, the outer sheath balloon 608 is expanded to engage the cervical canal wall while the uterine balloon 606 fills the uterine cavity and engages with the cornual regions of the uterus 604. In one embodiment, the balloon 606 may not conform or fill the entire uterine cavity but it is configured to provide a full engagement with the cornual regions of the uterus without filling the entire uterine cavity.

The uterine balloon 606 has a triangular or heart-shaped configuration when inflated. The uterine cavity is expandable so that it may stretch or adjust to the inflated uterine balloon 606 so that two sealed regions 620a, 620b are created. The sealed regions 620a, 620b created are air tight or fluid tight if the occluded areas 614 are not patent. The uterine balloon 606 engages the fundus and the cornua of the uterus to create a sealed region. As mentioned, the uterine balloon 606 is inflatable with air, water, saline solution, or any other known fluid.

The uterine balloon 606 also includes a first tube 616 and a second tube 618 within the inflated balloon 606. The first tube 616 extends from a distal end of the catheter 602 to an upper corner region of the uterine balloon 606 to align with the tubal ostia. The first tube 616 includes a distal opening into the first sealed region 620a of the uterus 604. The second tube 618 includes a distal opening into the second sealed region 620b of the uterus 604 to align with the tubal ostia. It is understood that the first 616 and second tubes 618 may remain flush with an outer surface of the uterine balloon 606 or may extend beyond the outer surface of the uterine balloon 606 protruding into the sealed regions 620a, 620b. The first 616 and second tube 618 are coupled to lumens within the catheter 602, as will be described in further detail.

After the sealed regions 620a, 620b are created, a second air or fluid pressure source 622 creates a pressure within the first tube 616, second tube 618, and sealed regions 620a, 620b. In one embodiment, a hand pump provides the necessary pressure. In another embodiment, bio-adhesives (as previously described) may be strategically applied on the outer surface of the uterine balloon 606 to ensure the balloon 606 is engaged with the endometrium to create a sealed region.

Figure 7:
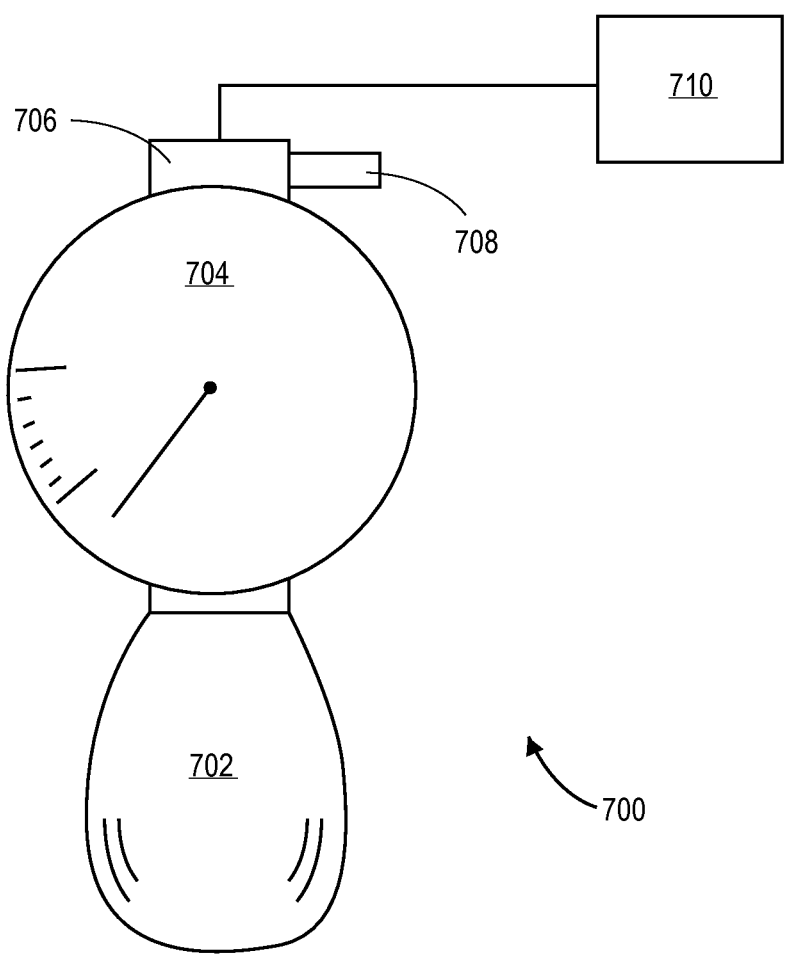
FIG. 7 shows a pump for providing pressure, according to one embodiment.

FIG. 7 shows an exemplary hand pump 700 for providing a pressure to the sealed regions 620a, 620b. The hand pump 700 includes a pump handle 702, a dial 704, a connecting piece 706, and a relief valve 708. The pump handle 702 is made of an elastic material such as rubber or silicone that compresses air when a user closes his or her grip. When a user releases his or her grip, the handle 702 returns to an initial uncompressed state. The dial 704 indicates to the user how much pressure is created within the sealed regions 620a, 620b. In one embodiment, a minimum pressure of 50 mmHg is provided or a maximum of 350 mmHg. An ideal pressure range is 90-120 mmHg to determine whether the fallopian tube is successfully occluded. A check valve 708 is connected with the hand pump 700 to allow excess pressure to escape when a predetermined value is reached. For example, in one embodiment, the check valve can be configured to release pressure above 350 mmHg to opening a fallopian tube or dislodging an implant. Therefore, when the user squeezes the pump handle 702 when the dial is reading 350 mmHg, the check valve releases any excess pressure. The connecting piece 706 is connected to a catheter 710. The catheter 710 can be of the same configuration and type of any catheter described in this application. Of course, if a fallopian tube is patent, the dial 704 will indicate a pressure drop so the user will know the regions 620a, 620b are not sealed. It is understood that negative or positive pressure can be applied by the hand pump 700 and the pump may be an automatic pump, according to one embodiment.

Figure 8A:
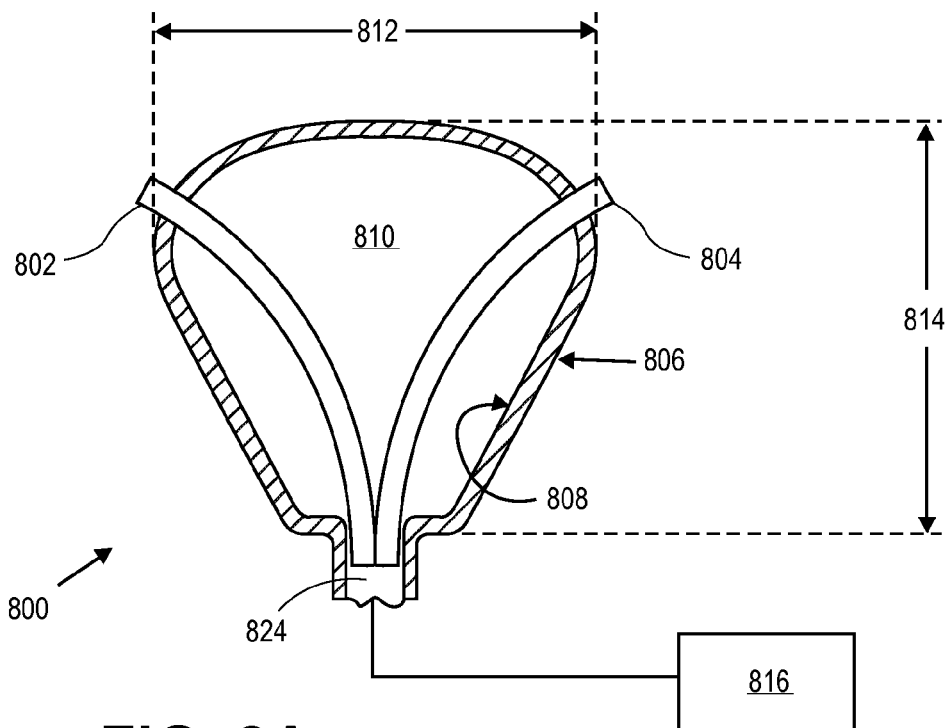
FIGS. 8A and 8B show cross sections of various embodiments of devices which may be used to determine if a fallopian tube is fully occluded.

FIG. 8A illustrates an exemplary embodiment of a uterine balloon 800 similar to the one shown in FIG. 6B. The first 802 and second 804 tubes are shown protruding slightly beyond an outer surface 806 of the uterine balloon 800. The inner wall 808 of the uterine balloon 800 defines an inflation cavity 810 where the air, water, saline, or other liquid fills the balloon 800 for inflation. The balloon 800 can be made from an elastic material such as silicone, latex, urethane, and other known flexible polymers. In one embodiment, the uterine balloon 800 is slightly larger than a typical uterus size. In one embodiment, the balloon 800 has an inflated width dimension 812 of 1.6-3.0 cm depending on the size of a patient's uterus. In another embodiment, the inflated width dimension 812 is at least 3.0 cm to ensure the balloon seals and engages with the fundal width. In one embodiment, the balloon 800 has an inflated length dimension 814 of 5-8 cm. In another embodiment, the inflated length dimension 814 is at least 8 cm to ensure the balloon seals and engages the uterus length. In yet another embodiment, the balloon can have an inflated width in a range from about 3-4 cm, a height in a range of about 5-7 cm, and a depth range of about 1-1.5 cm. A pressure of about 150-250 mmHg can be used to inflate the balloon.

As previously mentioned, the first 802 and second 804 tubes can be individually connected with a pressure source 816 such as the hand pump and gauge described in FIG. 7. The advantage of having an individual tube and gauge connection is that each fallopian tube can be verified independently of the other fallopian tube. In one embodiment, a different pressure is provided in the first tube 802 and second tube 804 so that the individual verification of each tube can be easily achieved. In one embodiment, more than one hand pump or gauge 816 can be connected with the balloon 800.

The first 802 and second 804 tubes can be made from a material including nylon, Teflon, silicone, tygon, polyethylene, and any other known flexible polymer. In one embodiment, the tubal openings can be in the range of about 0.1-0.3 cm.

Figure 8B:
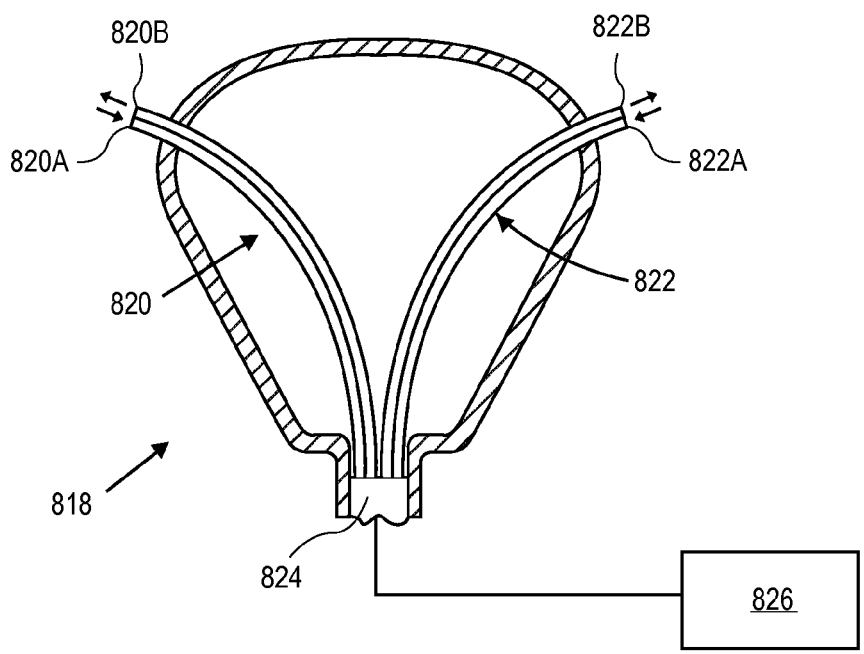

FIG. 8B illustrates another embodiment of a uterine balloon 818 having the same shape and dimensions as described above. The uterine balloon 818 includes a first pair of tubes 820 and a second pair of tubes 822 extending from a distal end of the catheter 824 to a respective sealed region in alignment with a tubal ostia. The first 820 and second pair of tubes 822 together form a Y-shape as previously described.

The first pair of tubes 820 include a first lumen 820a and a second lumen 820b. As described in FIG. 3A, a negative pressure is applied through the first lumen 820a within the sealed portion of the cornua. Distension fluid is evacuated from the sealed portion and measured using a measuring device 826 such as a marked syringe. It is understood that a separate syringe may be provided for each individual lumen or the same single syringe may be movable between each lumen. Again, a small amount of fluid can be evacuated such as 1 cc or less.

The second lumen 820b can supply a second fluid to replace the distension fluid. The volume of the second fluid applied is measured to determine if it is greater than the amount of distension fluid removed. As previously mentioned, if the volumes are equal or close (within 10%), the fallopian tube is determined to be positively occluded by the occlusion device.

On the other hand, if the volume of the second fluid is significantly greater than the amount removed, the second fluid is assumed to have leaked past the utero-tubal junction and occlusion device as previously described.

The second pair of tubes 822 include a first lumen 822a for removing distension fluid and a second lumen 822b for replacing the fluid. The second pair of tubes 822 operate in the exact same manner as described above with respect to the first pair of tubes 820.

Figure 9A:
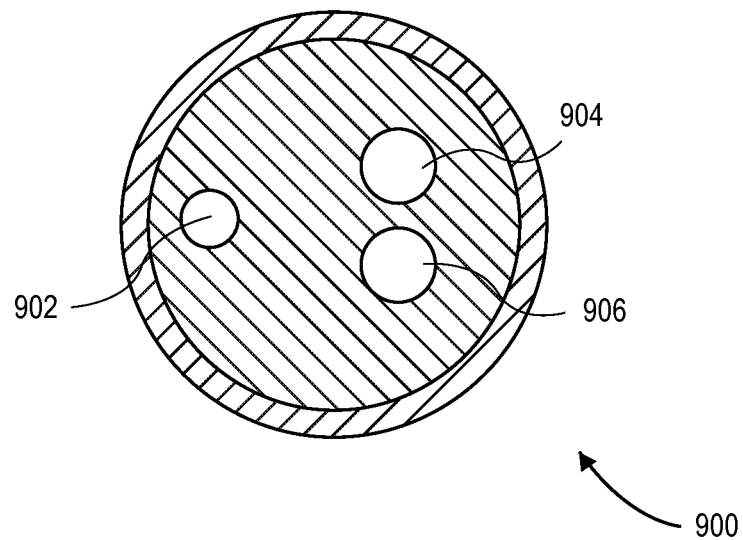
FIGS. 9A-9D show catheter cross sections of various embodiments used to determine if a fallopian tube is fully occluded.

FIGS. 9A-9D illustrate various catheter cross-sectional views that may be implemented in any of the embodiments previously discussed. FIG. 9A illustrates a catheter cross-section embodiment having a first lumen 902, a second lumen 904 and a third lumen 906 within the outer sheath. In one embodiment, the first lumen 902 is used to deliver air, fluid, saline, or any gas or liquid to inflate an outer sheath balloon 508, 608 or end balloon 506, 606. In addition, the first lumen 902 may be used to evacuate or vacuum the air or fluid. In one embodiment, the second 904 and third 906 lumen can be connected to inner catheters 504, 616 or the inner catheters can be located within the second and third lumen.

Figure 9B:
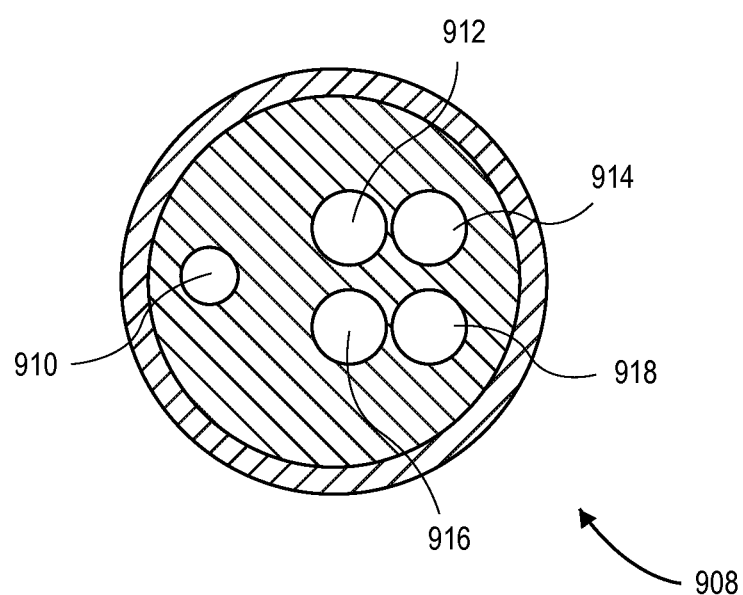

FIG. 9B shows another embodiment 908 having a first lumen 910, a second lumen 912, a third lumen 914, a fourth lumen 916, and a fifth lumen 918. Again, the first lumen 902 provides air or fluid to the balloons and may also evacuate or vacuum the air or fluid. The second 912 and third 914 lumens operate to evacuate a distension fluid from respective catheters, as previously described. The fourth 916 and fifth 918 lumens allow a replacement fluid to be injected into a sealed region, as previously described.

Figure 9C:
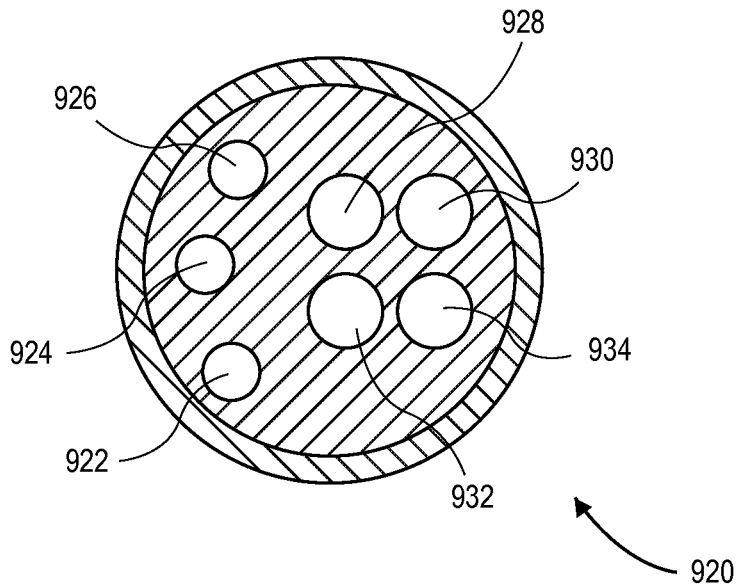

FIG. 9C shows yet another cross-sectional embodiment 920 having a first lumen 922, a second lumen 924, a third lumen 926, a fourth lumen 928, a fifth lumen 930, a sixth lumen 932, and a seventh lumen 934. The first lumen 922 acts primarily as a vacuum source while the second lumen 924 operates to fill the outer sheath balloon with air or fluid. The third lumen 926 primarily operates to fill the end balloon portions or uterine balloon with air or fluid. The fourth lumen 928 and fifth lumen 930 operate to vacuum or evacuate a distension fluid. The sixth 932 and seventh lumen 934 operate to inject a second fluid into the sealed region as previously described.

Figure 9D:
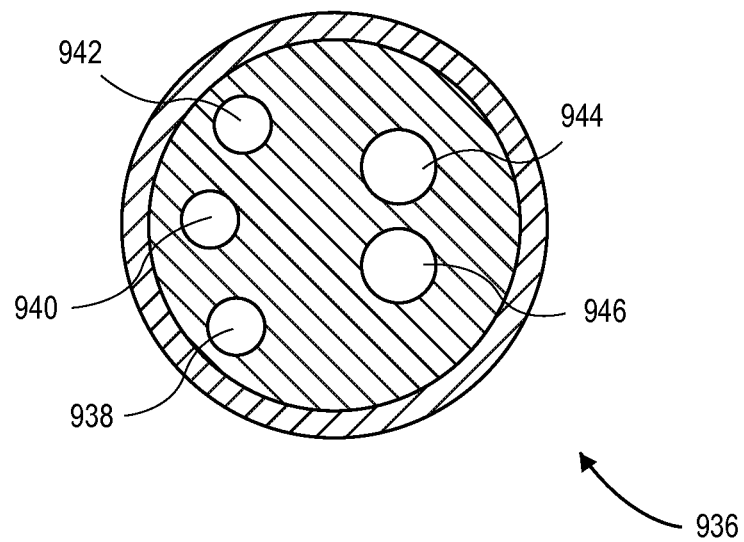

FIG. 9D shows another embodiment 936 having a first lumen 938, a second lumen 940, a third lumen 942, a fourth lumen 944, and a fifth lumen 946. The first 938, second 940, and third lumen 942 operate in the same manner as the embodiment described in FIG. 9C. The fourth 944 and fifth 946 lumen are provided to supply a monitoring pressure to the sealed region to determine if a respective fallopian tube is patent. The fourth lumen 944 correlates to one sealed region and the fifth lumen 946 correlates to a second sealed region of the cornua.

Although the lumens show are generally a circular shape, it is understood that the lumen passages can be a variety of cross-sectional shapes including semi-circles, squares, rectangles and any other known shape for delivering air or fluid to a cornua for determining whether a fallopian tube is occluded.

A significant advantage of the embodiments of the present invention is that the fallopian tubes can be tested for patency either individually or simultaneously. Having both cornual regions tested simultaneously results in reduced testing time and minimizes patient discomfort.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed:

1. A method to determine fallopian tube occlusion comprising:
    distending a uterus with a first fluid, the uterus including a first cornua of a first fallopian tube and a second cornua of a second fallopian tube;
    coupling a device to the first and second cornua to fluidly separate a corresponding first and second sealed portions of the first and second cornua from the remainder of the distended uterus;
    evacuating a first volume of the first fluid from the first sealed portion, and evacuating a second volume of the first fluid from the second sealed portion;
    measuring the first volume of the first fluid, and measuring the second volume of the first fluid;
    supplying a second fluid to the first and second sealed portions;
    measuring a third volume of the second fluid supplied to the first sealed portion, and measuring a fourth volume of the second fluid supplied to the second sealed portion;
    comparing the first volume of the first fluid to the third volume of the second fluid to determine if the first fallopian tube is occluded, and comparing the second volume of the first fluid to the fourth volume of the fourth fluid to determine if the second fallopian tube is occluded.

2. The method of claim 1, wherein the first fallopian tube is determined to be occluded if the third volume is within 10% of the first volume, and the second fallopian tube is determined to be occluded if the fourth volume is within 10% of the second volume.

3. The method of claim 1, wherein measuring the first and second volumes comprises measuring with a marked syringe.

4. The method of claim 1, wherein measuring the first volume comprises measuring 1 cc or less, and measuring the second volume comprises measuring 1 cc or less.

5. The method of claim 1, further comprising visually confirming that the second fluid does not leak into the first fluid in the remainder of the distended uterus.

6. The method of claim 1, wherein coupling the device to the first and second cornua to fluidly separate the corresponding first and second sealed portions of the first and second cornua from the remainder of the distended uterus comprises:
    expanding a first balloon end portion of a first catheter against the first cornua, and expanding a second balloon end portion of a second catheter against the second cornua.

7. The method of claim 6, further comprising expanding the first and second balloon end portions with a single air or fluid source.

8. The method of claim 6, further comprising expanding the first and second balloon end portions with separate air or fluid sources.

9. The method of claim 6, wherein coupling the device to the first and second cornua to fluidly separate the corresponding first and second sealed portions of the first and second cornua from the remainder of the distended uterus comprises:
    expanding a spring mechanism to form an open Y-position with the first and second catheters.

10. The method of claim 6, further comprising applying a vacuum to a first vacuum cavity in the first balloon end portion and to a second vacuum cavity in the second balloon end portion to engage the first and second cornua.

11. The method of claim 1, wherein coupling the device to the first and second cornua to fluidly separate the corresponding first and second sealed portions of the first and second cornua from the remainder of the distended uterus comprises:
    expanding a uterine balloon and engaging the first and second cornua with the expanded uterine balloon.

12. The method of claim 1, wherein the second fluid is not soluble with the first fluid.

* * * * *